United States Patent [19]

Prendin et al.

[11] Patent Number: 5,719,300
[45] Date of Patent: Feb. 17, 1998

[54] PROCESS FOR THE PREPARATION OF GESTODENE

[75] Inventors: Rino Prendin, Castellanza; Silvio Pirovano, Gallarate, both of Italy

[73] Assignee: Industriale Chimica S.R.L., Milan, Italy

[21] Appl. No.: 515,822

[22] Filed: Aug. 16, 1995

[30] Foreign Application Priority Data

Sep. 9, 1994 [IT] Italy .................... MI94A1846

[51] Int. Cl.$^6$ .................................... C07J 5/00
[52] U.S. Cl. ........................................ 552/648
[58] Field of Search .......................... 552/648, 646

[56] References Cited

U.S. PATENT DOCUMENTS

| | | | |
|---|---|---|---|
| 3,876,670 | 4/1975 | Coombs et al. | 260/397.45 |
| 4,081,537 | 3/1978 | Hofmeister et al. | 424/238 |
| 4,719,054 | 1/1988 | Hofmeister et al. | 260/397.4 |
| 4,923,640 | 5/1990 | Bohlmann et al. | 552/625 |

FOREIGN PATENT DOCUMENTS

| | | |
|---|---|---|
| 1345339 | 1/1974 | United Kingdom . |
| 9406819 | 3/1994 | WIPO . |

OTHER PUBLICATIONS

Chen et al., "Synthesis of 17alpha– ethynyl–17beta–hydroxy–18–methylestra–delta 4,15–dien–3–one (gestodene)." Reproduction and Contraception, 15(3): 197–201, 1995.

Hofmeister, et al., "Syntheses of gestodene". Arzneimittel–Forschung/Drug Research, 36(1): 781–783, 1986.

Tetrahedron Letters, Nakamara et al. "Highly Stereoselective Formation of Enol Silyl Ethers" No. 24, 2079–2082 (Jun. 1978).

JACS, Nakamura et al. "Quaternary Ammonium Enolates As Synthetic Intermediate", vol. 98, No. 8, 2346–2348 (1976).

Primary Examiner—José G. Dees
Assistant Examiner—Barbara Badio
Attorney, Agent, or Firm—Abelman, Frayne & Schwab

[57] ABSTRACT

Disclosed is a process for the preparation of Gestodene (formula I) from (-)estra-1,3,5(10),8-tetraen-3-methoxy-18-methyl-17β-hydroxy.

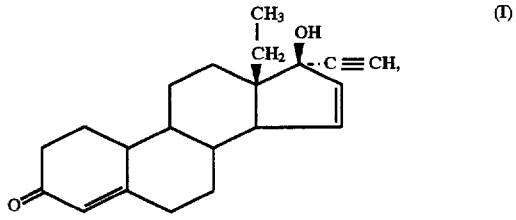

4 Claims, No Drawings

PROCESS FOR THE PREPARATION OF GESTODENE

Object of the present invention is a process for preparing Gestodene (17α-ethynil-17β-hydroxy-18-methyl-4,15-estradien-3-one) a drug well known for the progestinic activity, having structure formula:

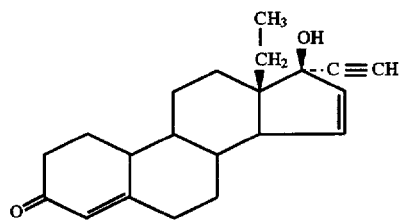

The compound (-)estra-1,3,5(10),8-tetraen-3 methoxy-18 methyl-17β-hydroxy with structure formula:

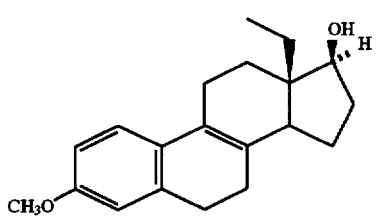

is used as starting product.

The process according to the invention in comparison with the known processes is new and original for the used starting product and for the sequence of the operative steps, some of which are substantially different from those of the known processes.

The process according to the invention shows on its whole, with respect to the known processes, remarkable advantages about the separation facility and the purity both of the intermediates and of the final product, as it will be pointed out in the following.

PRIOR ART

The preparation described by the base Patent of the "Gestodene" U.S. Pat. No. 4,081,537 consists substantially in the following steps:

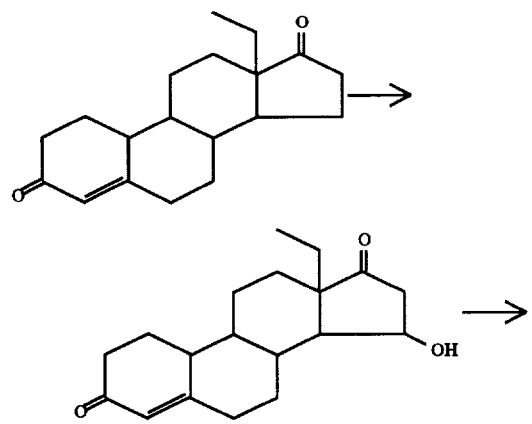

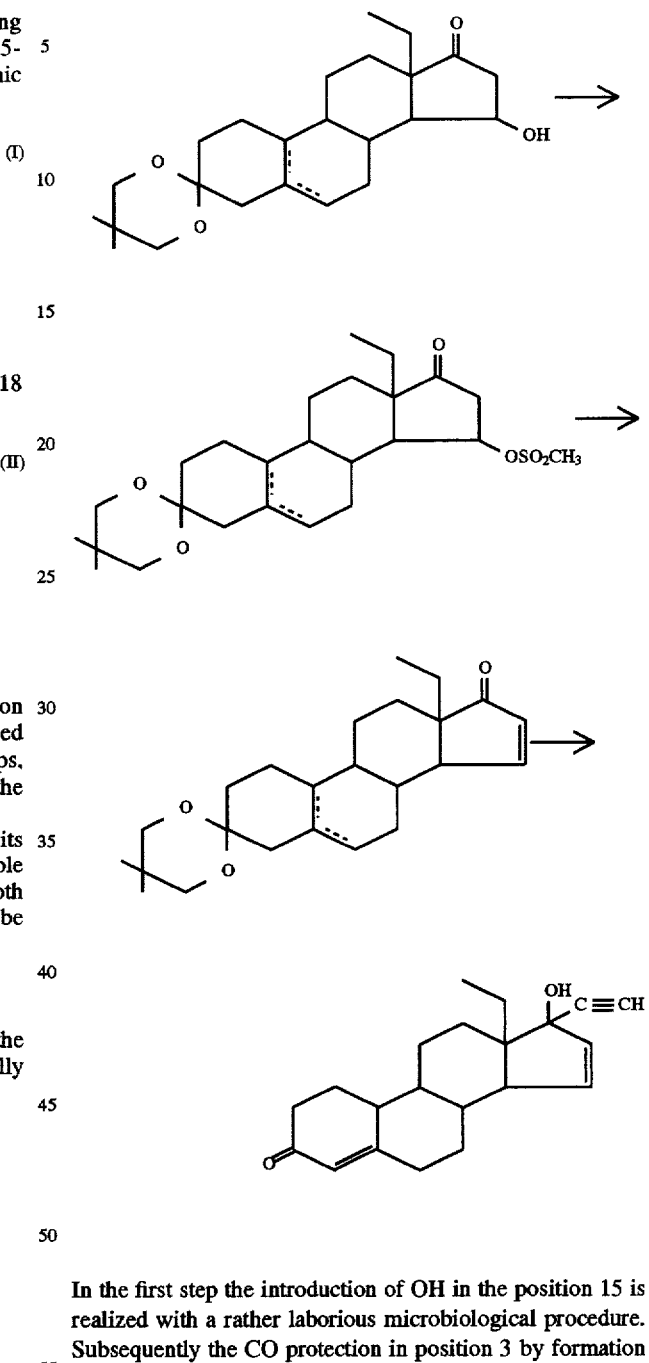

In the first step the introduction of OH in the position 15 is realized with a rather laborious microbiological procedure. Subsequently the CO protection in position 3 by formation of a ketal with 2,2 dimethyl-1,3-propanediol, the conversion of OH into methylsulphonyloxy group, the subsequent elimination of methyl sulphonic acid (dehydration) with formation of the double bond in 15–16 and at last the ethynylation in 17 and the elimination of the protective ketalic group in 3 are performed. In the U.S. Pat. No. 4,923,640 the synthesis of the Gestodene based on the following scheme is described:

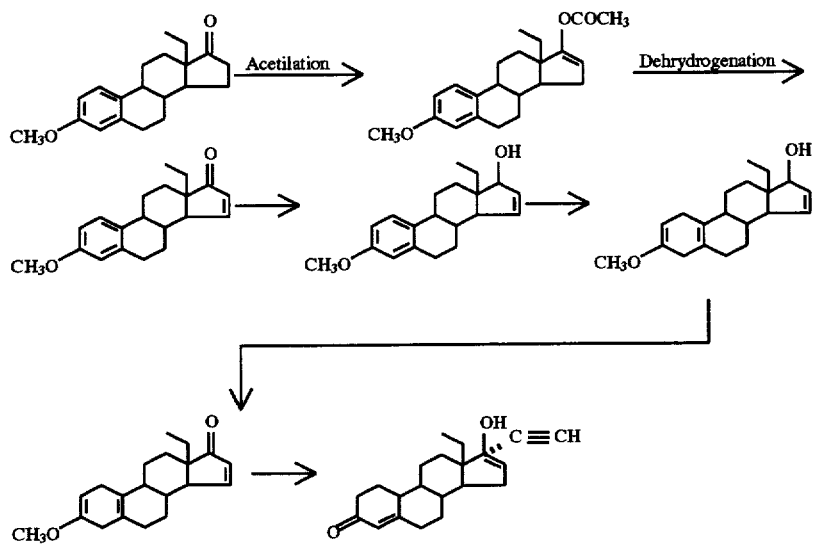

The first process (U.S. Pat. No. 4,081,537) is rather complex for the difficulty of functionalizing the position 15 or 16: the bromination in C16 involves the formation of by-products and so a low yield while the introduction of art hydroxyl in C15 is obtained by an expensive microbiological step.

The second process (U.S. Pat. No. 4,923,640) has the defect of introducing the double bond in 15–16 in a starting step of the synthesis; this double bond is always partially reduced every time that the molecule is in reducing conditions, as in the subsequent reduction to alcohol or during the reduction of the aromatic ring to cyclohexadienyl; this fact implies a difficulty of the purification from the corresponding saturated product and in conclusion a reduction of the global yield.

PROCESS ACCORDING TO THE INVENTION

As it has already been specified from the beginning the starting product in the process according to the invention is that having formula:

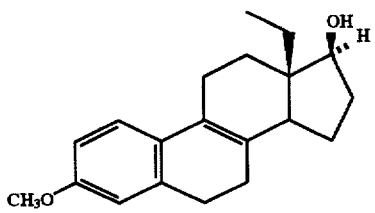 (II)

It may be prepared according to the method described in J.C.S. 4472 (1964) H. Smitt et al. starting from 2-ethyl-cyclopentane-1,3-dione and 1-vinyl-1-hydroxy-1,2,3,4-tetrahydro-6 methoxy-naphthalene obtaining the racemic mixture (±)estra-1,3,5(10),8-tetraen-3-methoxy-18-methyl-17β-hydroxy from which the isomer levo(-)estra-1,3,5(10),8 tetraen-3-methoxy-18-methyl-17β-hydroxy is obtained operating according to Chem. Pharm. Bull. 13 no. 11, 1289 (1965) K. Hiraga.

In the step 1 of the process according to the invention it is hydrogenated with elimination of the double bond in 8 by metallic Li dissolved in liquid $NH_3$, at a low temperature, in a reaction solvent preferably consisting of tetrahydrofuran (THF). Also other polar apotric solvents as diethyl ether, dioxane, ethylene glycol dimethyl ether are possible.

The operation is performed at a temperature not higher than –55° C. in presence of aniline.

The compound:

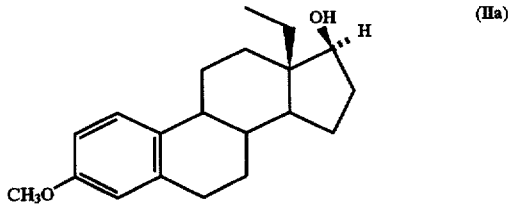 (IIa)

is obtained.

In the subsequent step 2 the reduction of the aromatic ring to cyclohexadienyl by reaction with metallic Li dissolved in liquid $NH_3$, in presence of ter.butanol with reaction solvent THF is done. Also other reaction solvents as diethyl ether, dioxane, ethylene glycol dimethyl ether are possible.

Moreover the ter.butanol may be substituted by ethanol, methanol, ethylene glycol monomethyl ether. This is done between –55° C. and –60° C.

The compound:

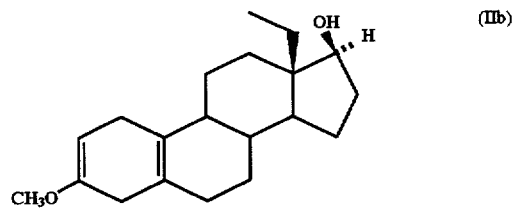 (IIb)

is obtained.

In the step 3 the methoxy-group in position 3 is substituted reconstituting the >C=O group by reaction of hydrolysis carried out in presence of aqueous HCl in THF as reaction solvent, and in consequence conversion of the enol to the ketonic form and at the same time transposition of the double bond from 5–10 to 4–5 (formation of a conjugated dienic structure). The ethyl-acetate or the methanol may be used as reaction solvent.

The compound:

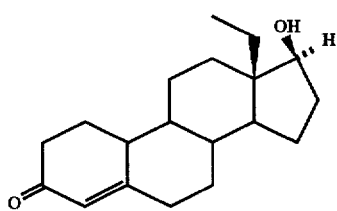

(III)

is obtained.

In the step 4 the protection of the ketonic group in 3 is realized converting it in the ethylene acetal group (or other acetal group) by reaction with ethylene glycol (or other glycol) catalyzed with paratoluensulphonic acid and with azeotropic dehydration in presence of toluene. At the same time the double bond transposition in the position 5–6 or 5–10 occurs with the formation of the two isomers:

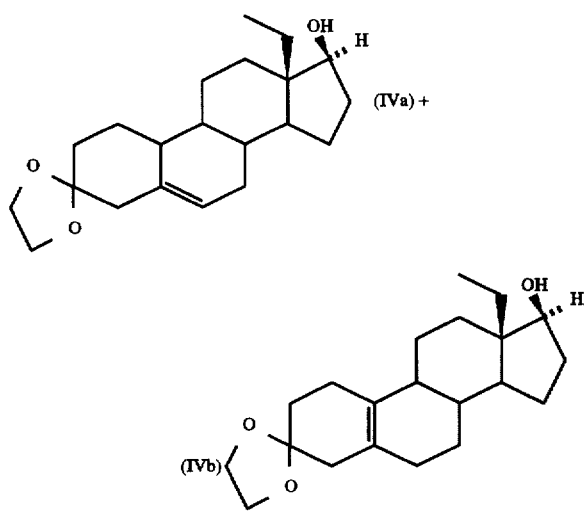

(IVa)+

(IVb)

In the step 5 the hydroxyl in position 17 is converted into a ketonic group by reaction with isopropylate of Al in presence of methyl ethyl ketone with toluene or other suitable solvent as reaction solvent according to the Oppenauer's method (Rec. Tray. Chi. 56,137 (1937); Org. React. 6,207 (1951), J.O.C. 28,1431 (1963)).

This is done at the solvent boiling point.

This oxidation may be obtained also with many other oxidants as: N—Br(Cl,I)succinimide, manganese dioxide, Ru tetraoxide, potassium permanganate, sodium hypochlorite, dichloro dicyanobenzoquinone even if the most specific ones are the alcoholates of aluminium (isopropylate, terbutylate) with methyl ethyl ketone.

The two isomers:

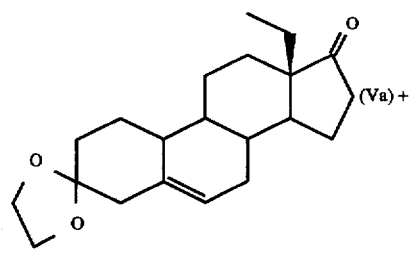

(Va)+

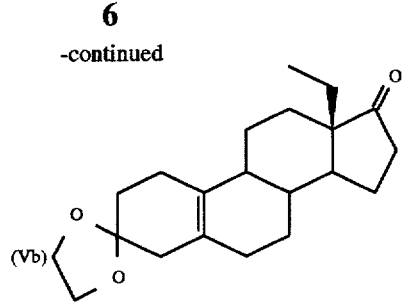

(Vb)

are obtained.

In the step 6 the mixture of the two isomers Va and Vb is submitted to silanization for the protection of the hydroxyl in position 17 (deriving from the enolization of the 17-keto derivative of the formula V).

The silanization is preferably done with ethyl trimethylsilyl acetate in presence of tetrabutyl ammonium fluoride as catalyst.

In a second phase including the reaction with Pd(II) acetate (as oxidant) the ketonic group is restored and a double bond is realized in position 15–16.

In this way the compound in the two isomeric forms (corresponding to the starting isomers):

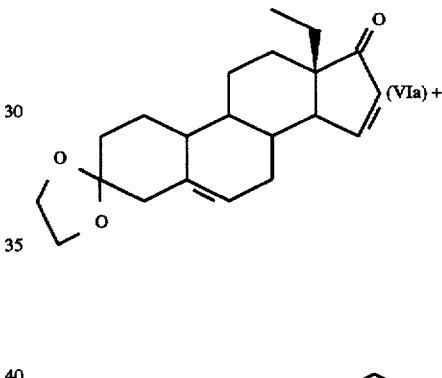

(VIa)+

(VIb)

is obtained.

In the subsequent step 7 the ethynylation is realized in position 17 by reaction at low temperature with Li acetylide complexed with ethylenedivine in presence of THF or other suitable solvent, between –5° C. and the room temperature.

The product by the Fluka having formula Li C↑CH H₂NCH₂CH₂NH₂ is preferably used.

The compound in the two isomeric forms (corresponding to the starting isomers):

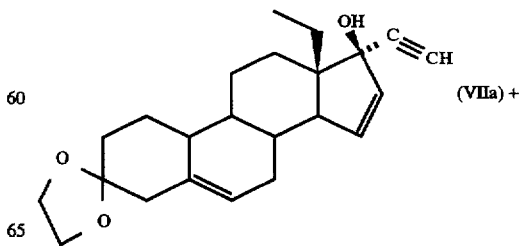

(VIIa)+

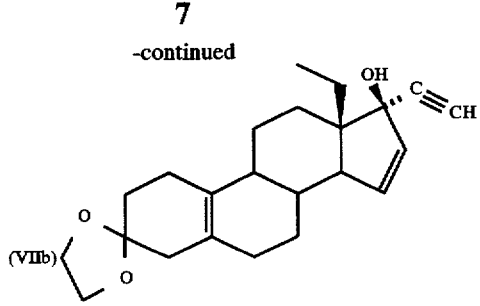

is obtained.

Finally in the step 8 the compound VII (mixture of the isomers a+b) is submitted to hydrolysis with aqueous HCl in THF at 45°–50° C.

The final product "Gestodene" is so obtained after to the reinstatement of the >CO group in position 3 and consequent transposition of the double bond from the position 5–6 or 5–10 to the position 4–5.

From the mixture of the isomers VIIa and VIIb the compound "Gestodene" having formula

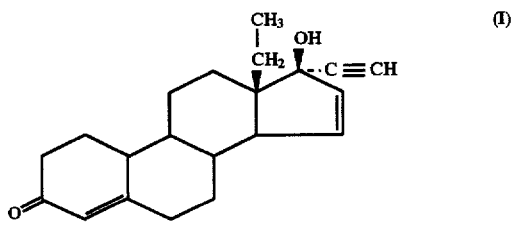

is obtained.

In the process according to the invention it is considerable the fact that either the intermediates a) with double bond in 5–6 or the corresponding isomers b) with double bond in 5–10, are finally converted in the desired product, the Gestodene.

For this reason the formation of the two isomers does not imply problems of separation or decrease of final yield. In the process according to the invention in general the intermediate products as such as obtained in the former operative step may be used without need to isolate them to the pure state by separation of secondary products possibly present.

With respect to the process known from the U.S. Pat. No. 4,923,640 the process according to the invention is characterized by the fact that the introduction of the double bond in 15–16 occurs in the last but one phase of the process while according to the known process where said double bond is already introduced in the 2nd step, each time that the product is in reducing reaction medium this double bond is partially reduced and the final product is separable from the corresponding saturated compound with great difficulty.

Another difference with the aforesaid known process is that in the process according to the invention the ketonic function in 3 is protected as ethylene ketal: this causes the displacement of the double bond in 5–6 (or 5–10) with stabilization of the first ring that otherwise (in the cyclohexadienyl structure) is very sensible to the oxidation with return to the aromatic structure. The protection in form of methoxy-group according to the aforesaid known process in fact implies a partial aromatization of the ring when it must be worked in oxidant conditions for the introduction of the double bond in 15–16.

The intermediate described in the process according to the present invention: 3,3-ethylendioxy-18-methyl-5,15 estradien-17-one (see example 6) is a new product, not described in literature: a similar product the 3,3(2',2'-dimethyl-1+,3'-propylen) dioxy is described by the U.S. Pat. No. 4,081,537.

The reported examples are showing and not limiting the possibilities of the process realization according to the invention.

EXAMPLE 1

Synthesis of the Intermediate IIa

Estra-1,3,5(10)-trien-3-methoxy-18-methyl-17β-hydroxy.

A solution consisting of 200 g of (-)estra-1,3,5(10),8-tetraen-3-methoxy-18-methyl-17β-hydroxy, 5,7 liters of tetrahydrofuran, 1,78 liters of aniline and 20 mg of metallic lithium, is loaded in an anhydrous reactor under nitrogen, containing 5 liters of liquid ammonia, maintaining the temperature under –55° C.

Then 28 g of metallic lithium are added portion by portion, maintaining the temperature between –60° and –55° C. It is left under agitation for two hours, then the reaction mixture is turned off pouring it on a mixture consisting of 667 g of triethylamine hydrochloride and 2 liters of tetra hydrofuran, previously cooled to –60° C.

At the end of the turning off 60 liters of water and ice are added and it is extracted with toluene.

The organic phase is washed with acidic water for eliminating the aniline, dehydrated on sodium sulfate, filtered and dry concentrated. The residue is crystallized by isopropanol.

184 g of intermediate IIa are obtained.

EXAMPLE 2

Synthesis of the Intermediate IIb

Estra-2,5(10)-dien-3-methoxy-18-methyl-17β-hydroxy

In a flask containing 1 liter of liquid ammonia and maintained at –50° C., a solution of 38 g (0,126 moles) of intermediate IIa dissolved in 2200 ml of tetrahydrofuran distilled on sodium and 775 ml of tert-butanol is dropped.

Maintaining the temperature at –60° C. 25 g (3,6 moles) of metallic lithium are loaded portion by portion till the persisting of a deep blue solution.

When the reaction is complete it is turned off by cooling at –65° C. and adding portion by portion 545 g (3,96 moles) of triethylamine hydrochloride. The ammonia is then left to evaporate.

The residuum is suspended in water and extracted with toluene. The organic phase is washed first with acidic water, then with water till neutral pH. The phases are separated and the organic one is dehydrated on sodium sulphate, filtered and dry concentrated.

43 g of raw intermediate IIb are obtained.

EXAMPLE 3

Synthesis of the Intermediate

Estra-4-en-3-one-18-methyl-17β-hydroxy 41 g of raw intermediate IIb obtained from the former reaction (theoretical 56 g=0.12 moles) are dissolved in 1600 ml of tetrahydrofuran.

Maintaining the temperature under 20° C. and working in an inert atmosphere, 150 ml of hydrochloric acid diluted 1:1

(0.78 moles) are dropped. It is warmed to 30° C. and it is maintained to this temperature for about 1 hour.

Then it is unloaded in 500 ml of water and it is extracted with 500 ml of toluene.

The organic phase is washed with an aqueous solution of sodium bicarbonate at 10%, then with water till a neutral pH. The phases are separated and the organic one is dehydrated on sodium sulphate, filtered and dry concentrated. 38,5 g of a white solid which are washed in a mixture 1:1 hexane, ether, are obtained.

It is cooled with a bath of water and ice and filtered.

28,20 g of intermediate III, with the following characteristics, are obtained: purity HPLC 98,7% (column: Merck Select B, 12.5 cm×4 mm, 5μ; flux 1 ml/min, detector UV to 220 nm; mobile phase: methyl alcohol-eptansulfonic acid/diethylamine/water to pH3 70:30 v/v); $^1$H NMR (CDCl$_3$) δ 1,00 (t, 3H CH$_3$, J$_{CH3-CH2}$=7,3 Hz), 1,41 (q, 2H CH$_2$, J$_{CH3-CH2}$=7,3 Hz), 0,75–2,5 (m, 21H), 3, 72 (m, 1H, H-17), 5,80 (s, 1H, H-4); mass peaks m/z 288 (molecular), 270 (—H$_2$O), 259 (—CH$_2$CH$_3$).

EXAMPLE 4

Synthesis of the Intermediate IV 3,3-ethylendioxy-estra-5-en-18-methyl-17β-hydroxy, +3,3 ethylen-dioxy-estra-5(10)-en-18-methyl-17β-hydroxy.

In the flask with a Marcusson's distiller 7,8 g of para-toluen sulphonic monohydrate acid (0,04 moles) and 1500 ml of toluene are loaded. It is distilled for dehydrating, then 27 g of intermediate III (0,094 moles) and 314 ml of ethylene glycol (5,625 moles) are loaded at room temperature. It is warmed at 110° C., distilling the toluene and the water produced in the reaction.

The distilled toluene is reinstated for a final volume of about 1200 ml.

When the reaction is finished (control TLC: eluent hexane-ethylacetate 1:1, detector UV and vanillin 1% in sulphuric acid) the reaction mixture is unloaded in 1000 ml of a 10% solution of sodium bicarbonate in water, previously cooled at 0° C.

It is washed for 20 minutes and then the phases are separated, the organic phase is washed with water till neutral pH.

The organic phase is then dehydrated on sodium sulphate, filtered and dry concentrated.

32,8 g of an amorphous solid, consisting of the mixture of the two isomers IVa and IVb, are obtained.

EXAMPLE 5

Synthesis of the Intermediate V 3,3-ethylendioxy-estra-5-en-17-one-18-methyl, +3, 3- ethylendioxy-estra-5(10)-en-17-one-18-methyl.

In a flask with a Marcusson's distiller 30 g of intermediate IV (0,09 moles) in mixture form of the two isomers, 225 ml of 2-butanone and 1000 ml of toluene are loaded. It is made inert with nitrogen, then 25,7 g of aluminium isopropylate (0,126) dissolved in 210 ml of toluene are dropped.

It is then warmed to reflux distilling the solvent and reinstating with 2-butanone.

After 3 hours and 30 minutes reflux (total solvent distilled=400 cc), it is cooled to room temperature, it is poured in a frozen aqueous solution of 10% sodium bicarbonate and it is shaked for 20 minutes. The salts of aluminium are filtered on celite then the phases are separated. The aqueous phase is extracted again for two times with 450 ml of toluene.

The organic phases are put together and washed with a solution of 10% sodium bicarbonate in water and then only with water till a neutral pH. The organic phase is then dehydrated on sodium sulphate, filtered and dry concentrated.

32,5 g of yellow oil are obtained.

The residuum, taken up again with 40 ml of ethyl ether, crystallizes giving a white solid, which washed in hexane, filtered and dried, gives 12,2 g of a crystalline solid consisting of a mixture about 6:4 of the two isomers Va and Vb.

The product has the following analitical characteristics: $^1$H NMR (CDCl$_3$) δ0,7–0,8 (2 t superimposed of Va and Vb, 3H, CH$_3$), 0,9–2,5 (m, 22H), 3,9–4,0 (m, 4H, CH$_2$ cyclic ketal), 5,45 (m, 0,6H, H-6 of Va); mass peaks m/z 330 (molecular), 301 (—CH$_2$CH$_3$); mass (FAB) M+1 331; melting point 115°–120° C.; IR spectrum C=O 1730 cm$^{-1}$.

Due to the fact that it is a mixture the rotating power has not been determined because it is little significant.

EXAMPLE 6

Synthesis of the Intermediate VI 3,3-ethylendioxy-estra-5,15-dien-17-one-18-methyl, +3,3-ethylen-dioxy-estra-5(10), 15-dien-17-one-18-methyl.

11 ml of 1M solution in THF of tetrabuthylammonium fluoride (11 moles) are loaded in a perfectly anhydrous flask, then they are dried applying a vacuum not lower than 0,5 mmHg and warming to 70° C.

They are left in these conditions for 30 minutes, then they are cooled to room temperature and, under nitrogen, 12 g of intermediate V in form of the two isomers mixture (0,036 moles) dissolved in 150 ml of tetrahydrofuran distilled on sodium are loaded.

30 ml of tetrahydrofuran are distilled, the room temperature is regained and 44 ml of ethyl trimethylsilyl acetate are added (0,24 moles).

It is warmed to 30°–35° C. for 6 hours.

When the reaction is finished it is cooled to room temperature and the reaction is turned off in a mixture consisting of 410 ml of 10% sodium bicarbonate in water and 185 ml of hexane.

It is extracted with toluene, the phases are separated, the organic phase is dehydrated on sodium sulphate, filtered and dry concentrated.

25 g of a yellow oil (silanized intermediate V) are obtained which are immediately dissolved in 735 ml of acetonitrile distilled on phosphorus pentoxide.

This solution, loaded in a perfectly anhydrous flask and under nitrogen, is warmed to 35°–40° C. and added with 12,1 g of palladium acetate (0,054 moles).

It is left to itself for a night.

Coal is added when the reaction is finished, it is shaked for 30 minutes, then it is filtered, it is treated with thioacetamide for completely removing the Pd and it is dry concentrated.

13,75 g of product VI as an oil are obtained.

A part of this oil, treated with methanol, crystallizes giving a crystalline solid consisting of a mixture about 7:3 of VIa and VIb with the following analitical characteristics: $^1$H NMR (CDCl$_3$) δ 0.7–0.8 (2 t overlapped of VIa and VIb, 3H, CH$_3$), 1.0–2.5 (m, 18H), 3.9–4.0 (m, CH$_2$ cyclic ketal), 5.48 (m, 0.7H, H-6 of VIa), 5.99 (m, 1H, H-15), 7.47 (d, 0.7H, H-16 of VIa), 7.54 (d, 0.3H, H-16 of VIb); mass (FAB) M+i 329; melting point 115°–120° C.; spectrum IR C=O 1705 cm$^{-1}$.

Due to the fact that it is a mixture the rotatory power has not been determined because it is little significant.

EXAMPLE 7

Synthesis of the Intermediate VII 3,3-ethylendioxy-estra-5,15-dien-18-methyl-17α-ethynyl-17β-hydroxy, +3,3-ethylendioxy-estra-5(10), 15-dien-18-methyl-17α-ethynyl-17β-hydroxy.

11 g of intermediate VI (0.0335 moles) and 550 ml of tetrahydrofuran distilled on sodium are loaded in a flask. It is cooled to –5° C. and, working under nitrogen, 15.4 g of lithium acetylide complexed with ethylendiamine (0.1675 moles) are added in about 10 minutes. It is allowed to return to room temperature and then it is unloaded in a solution formed by 31 g of ammonium chloride dissolved in 370 ml of water at 0° C.

It is shaked for 30 minutes, then it is extracted with toluene.

The phases are separated; the organic phase is dehydrated on sodium sulphate, filtered, and dry concentrated.

11.2 g of the intermediate VII are obtained. A sample of raw intermediate VII, crystallized by hexane, has given a crystalline solid mainly consisting of the isomer VIIb, with the following analytical characteristics: $^1$H NMR (CDCl$_3$) δ0.82 (t,3H,CH$_3$, J$_{CH3-CH2}$ 7.5 Hz), 1.1–2.4 (m, 19H), 2.61 (S, 1H, C=C—H), 3.9–4.0 (m, 4H, CH$_2$ cyclic ketal), 5.67 (q, 1H, H-15), 5.98 (q, 1H, H-16); rotatory power [α]$_D^{25}$= –113.5° C.=1% in CHCl$_3$: melting point: about 120° C.

Synthesis of the Gestodene

Estra-4,15-dien-3-one-18-methyl-17α-ethynyl-17β-hydroxy.

11 g of the intermediate VII dissolved in 500 ml of tetrahydrofuran are loaded in a flask.

40 ml of hydrochloric acid diluted 1:1 are dropped under nitrogen. It is then warmed to 45°–50° C. for 2 hours.

When the reaction is finished it is cooled and it is unloaded in a mixture of 17 g of sodium bicarbonate dissolved in 370 ml of water at 0° C.

It is extracted with toluene and the phases are separated. The organic phase is washed with an aqueous solution of sodium bicarbonate, then with water till neutral pH. The toluene is then dehydrated on sodium sulphate, filtered and dry concentrated.

About 8.7 g of solid are obtained which are chromatogaphated on 700 g of silica gel eluating with hexane/ethyl acetate 7:3.

The fractions containing the Gestodene have been reunited, dry concentrated and crystallized by ethyl acetate.

3.1 g of Gestodene are obtained with the following analytical characteristics:

$^1$H NMR (CDCl$_3$ δ0.91 (t, 3H, CH$_3$, J$_{CH3-CH2}$ 7 Hz), 1.0–2.6 (m, 18H), 2.63 (s, 1H, C=C—H), 5.73 (q, 1H, H-15), 5.84 (s, 1H, H-4),5.94 (q,1H, H-16); mass m/z 310 (molecular),281 (—CH$_2$CH$_3$), 255 (—H—C=C—H from 281); rotatory power [α]$_D^{25}$=–179.1° C.=1% in CHCl$_3$; melting point 199° C.; title HPLC 98.10% .

We claim:

1. Process for preparing 17α-ethynyl-17β-hydroxy-18-methyl-4,15 estradien-3-one (Gestodene) starting from (-) estra-1,3,5(10),8-tetraen-3-methyoxy-18-methyl-17β-hydroxy, comprising the following operative steps: a) reacting the starting compound with metallic Li dissolved i liquid NH$_3$, at a temperature not higher than –55° C., in a polar aprotic solvent and in the presence of aniline, resulting in the hydrogenation of the double bond in position 8, and consequent formation of an intermediate:

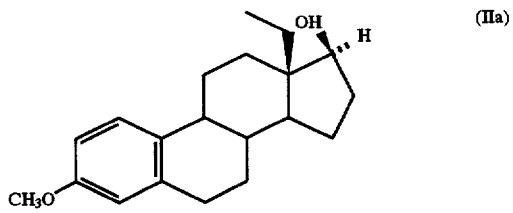

b) reacting the intermediate (IIa) with Li dissolved in liquid NH$_3$ in presence of an alkanol, in a polar aprotic solvent, at a temperature between –55° and –60° C. resulting in the hydrogenation of double bond in the aromatic ring, with formation of the intermediate:

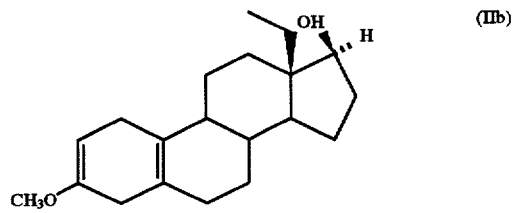

c) treating the intermediate IIb) with aqueous HCl in THF resulting in the hydrolysis of the CH$_3$O-group, the consequent conversion of the enol to the ketonic form and the spontaneous transposition of the double bond from 5(10) to 4(5) with formation of an intermediate:

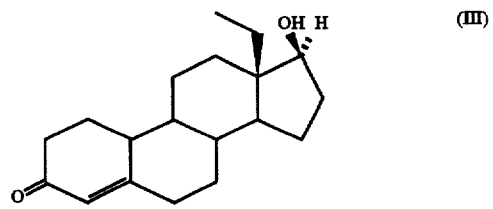

d) converting the ketonic group in position 3 of the intermediate (III) to an ethylenacetal group or other acetal group by reaction with glycol catalyzed with p-toluensulphonic acid and azeotropic dehydration in toluene, obtaining after the concomitant transposition of the double bond in 4(5) to the position 5(6) or 5(10) a mixture of two isomers:

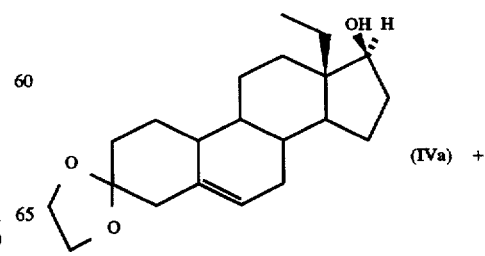

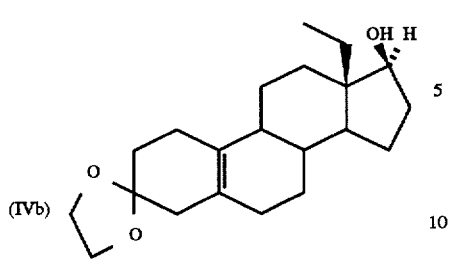

e) converting the hydroxyl in position 17 of the intermediate IV (mixture of the isomers a and b) to a ketonic group by reaction with a ketone in presence of alcoholate of Al in a reaction solvent, obtaining a mixture of the two isomers:

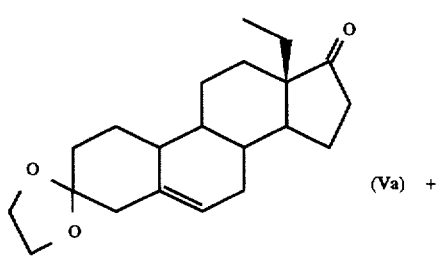

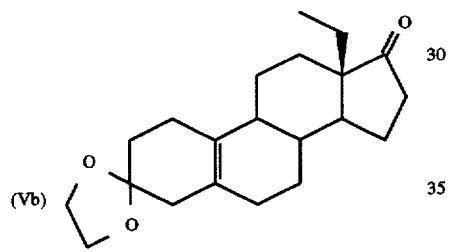

f) on the mixture of the isomers obtained in the former step the silanization of the hydroxyl in position 17, derived from enolization of the ketonic group, is performed by ethyl trimethylsilylacetate with tetrabutylammonium fluoride as catalyst, followed by oxidation with Pd(II) acetate and consequent formation of a double bond in 15(16) obtaining a mixture of the two isomers:

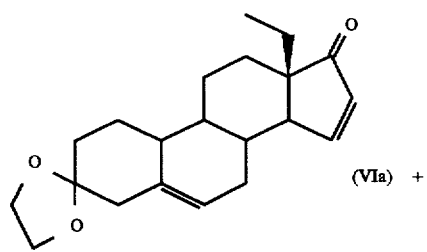

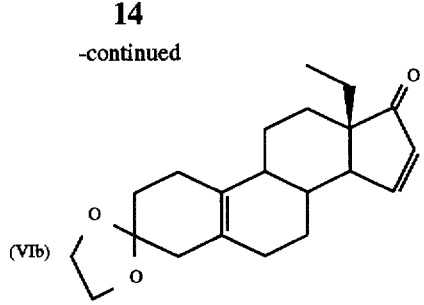

g) on the mixture of the isomers VIa+VIb the ethynylation is performed in position 17 by reaction with Li acetylide complexed with ethylenediamine in tetrahydrofuran, at room temperature or lower temperature till −5° C., obtaining in this way a mixture of two isomers:

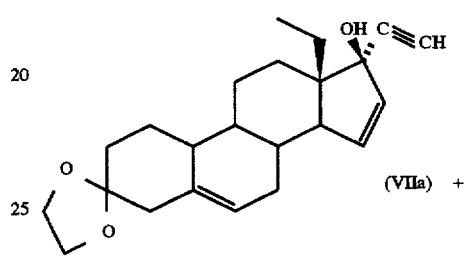

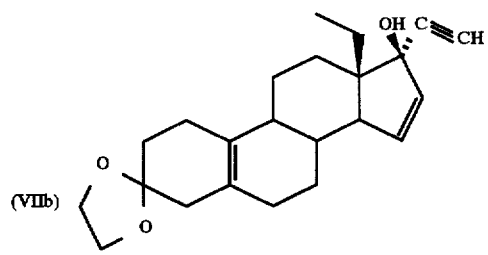

h) hydrolyzing the mixture of the isomers VIIa+VIIb is with aqueous HCl in tetrahydrofurane at 45°–50° C., resulting in the reinstatement of the ketonic group in position 3 and the transposition of the double bond of the position 5(6) or 5(10) to the position 4(5) with formation of the Gestodone compound.

2. A process is claimed in claim 1, wherein in the operative step a) the polar aprotic solvent used is selected from the group consisting of: THF, diethylether, dioxane, and ethylenglycol-dimethylether.

3. A process as claimed in claim 1, wherein in the operative step b) the alkanol used is selected from the group consisting of ter.butanol, methanol, ethanol, and ethylene glycol monomethyl ether and the reaction solvent used is selected from the group consisting of: THF, dioxane, diethylether, and ethylenglycol dimethylether.

4. A process as claimed in claim 1 wherein in the operative step e) the ketone used is methylethylketone and the alcoholate used is Al isopropylate.

* * * * *